(12) United States Patent
Rao et al.

(10) Patent No.: US 10,987,006 B2
(45) Date of Patent: Apr. 27, 2021

(54) WEARABLE COMPUTER WITH FITNESS MACHINE CONNECTIVITY FOR IMPROVED ACTIVITY MONITORING USING CALORIC EXPENDITURE MODELS

(71) Applicant: Apple Inc., Cupertino, CA (US)

(72) Inventors: Bharath Narasimha Rao, Mountain View, CA (US); Jennifer Strasser, San Jose, CA (US); Umamahesh Srinivas, Milpitas, CA (US); Kevin Sheridan, Menlo Park, CA (US); James Ochs, San Francisco, CA (US); Vinay R. Majjigi, Mountain View, CA (US); Karthik Jayaraman Raghuram, Mountain View, CA (US); Olivier Humblet, Palo Alto, CA (US); Jay Blahnik, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 35 days.

(21) Appl. No.: 16/129,664

(22) Filed: Sep. 12, 2018

(65) Prior Publication Data

US 2019/0008394 A1 Jan. 10, 2019

Related U.S. Application Data

(63) Continuation-in-part of application No. 15/613,131, filed on Jun. 2, 2017, now Pat. No. 10,814,167.
(Continued)

(51) Int. Cl.
*A61B 5/024* (2006.01)
*A61B 5/083* (2006.01)
(Continued)

(52) U.S. Cl.
CPC ............ *A61B 5/024* (2013.01); *A61B 5/0022* (2013.01); *A61B 5/02416* (2013.01);
(Continued)

(58) Field of Classification Search
CPC ... A61B 5/024; A61B 5/0022; A61B 5/02416; A61B 5/1118; A61B 5/6895;
(Continued)

(56) References Cited

U.S. PATENT DOCUMENTS 10,814,167 B2  10/2020  Blahnik
2013/0135115 A1  5/2013  Johnson et al.
(Continued)

FOREIGN PATENT DOCUMENTS

CN  101367011  2/2009
EP  2025369  2/2009
(Continued)

OTHER PUBLICATIONS

International Search Report and Written Opinion in International Application No. PCT/US2018/035493, dated Oct. 1, 2018, 14 pages.
(Continued)

*Primary Examiner* — Nicholas R Taylor
*Assistant Examiner* — Sanjoy Roy
(74) *Attorney, Agent, or Firm* — Fish & Richardson P.C.

(57) ABSTRACT

Embodiments are disclosed for a wireless wearable computer with fitness machine connectivity for improved activity monitoring using caloric expenditure models. In an embodiment, a method comprises: establishing, by a processor of a wireless wearable computer worn by a user, a wireless communication connection with a fitness machine; obtaining, by the processor using the communication connection, machine data from the fitness machine while the user is engaged in a workout session on the fitness machine;
(Continued)

obtaining, from a heart rate sensor of the wireless device, heart rate data of the user; determining, by the processor, a work rate caloric expenditure by applying a work rate calorie model to the machine data; determining, by the processor, a calibrated maximal oxygen consumption of the user based on the heart rate data and the work rate caloric expenditure; determining, by the processor, a heart rate caloric expenditure by applying a heart rate calorie model to the heart rate data and the calibrated maximal oxygen consumption of the user; and sending, by the processor to the fitness machine via the communication connection, at least one of the work rate caloric expenditure or the heart rate caloric expenditure.

18 Claims, 11 Drawing Sheets

Related U.S. Application Data

(60) Provisional application No. 62/697,386, filed on Jul. 12, 2018.

(51) Int. Cl.
*A61B 5/11* (2006.01)
*A63B 22/02* (2006.01)
*A61B 5/00* (2006.01)
*G01C 22/00* (2006.01)
*A61B 5/1455* (2006.01)
*A61B 5/1495* (2006.01)
*A61B 5/0531* (2021.01)
*A61B 5/02* (2006.01)
*A61B 5/01* (2006.01)

(52) U.S. Cl.
CPC .......... *A61B 5/0833* (2013.01); *A61B 5/1118* (2013.01); *A61B 5/1123* (2013.01); *A61B 5/1495* (2013.01); *A61B 5/14551* (2013.01); *A61B 5/4866* (2013.01); *A61B 5/6824* (2013.01); *A61B 5/6831* (2013.01); *A61B 5/6895* (2013.01); *A61B 5/7275* (2013.01); *A63B 22/02* (2013.01); *G01C 22/006* (2013.01); *A61B 5/01* (2013.01); *A61B 5/02* (2013.01); *A61B 5/0531* (2013.01); *A61B 2562/0219* (2013.01); *A63B 2230/06* (2013.01)

(58) Field of Classification Search
CPC ... A61B 5/1495; A61B 5/6831; A61B 5/7275; A61B 5/14551; A61B 5/4866; A61B 5/6824; G01C 22/006
See application file for complete search history.

(56) References Cited

U.S. PATENT DOCUMENTS

| | | |
|---|---|---|
| 2013/0178334 A1 | 7/2013 | Brammer |
| 2014/0197965 A1 | 7/2014 | Park et al. |
| 2014/0213920 A1* | 7/2014 | Lee .................. A61B 5/222 600/509 |
| 2014/0249661 A1* | 9/2014 | Dibenedetto .......... A44B 99/00 700/91 |
| 2014/0297217 A1* | 10/2014 | Yuen .................. G06F 19/3418 702/138 |
| 2015/0100141 A1* | 4/2015 | Hughes ................ A61B 5/6814 700/92 |
| 2015/0251055 A1 | 9/2015 | Ashby |
| 2015/0317438 A1 | 11/2015 | Ingrassia, Jr. et al. |
| 2016/0058302 A1 | 3/2016 | Jayaraman et al. |
| 2016/0058333 A1 | 3/2016 | Arnold et al. |
| 2016/0058372 A1* | 3/2016 | Raghuram ............ A61B 5/1118 600/595 |
| 2016/0107029 A1* | 4/2016 | Kim .................... A61B 5/0022 482/8 |
| 2016/0166156 A1 | 6/2016 | Yuen |
| 2017/0128778 A1 | 5/2017 | Sun et al. |
| 2017/0144025 A1 | 5/2017 | Abbondanza et al. |
| 2017/0173390 A1* | 6/2017 | Quy ..................... A61B 5/1112 |
| 2017/0216667 A1* | 8/2017 | Garvey ................ A61B 5/00 |
| 2017/0273619 A1* | 9/2017 | Alvarado .......... A61B 5/02444 |
| 2017/0333755 A1 | 11/2017 | Rider |
| 2018/0345077 A1 | 12/2018 | Blahnik |

FOREIGN PATENT DOCUMENTS

| | | |
|---|---|---|
| JP | 2009050699 | 3/2009 |
| JP | 2017513126 | 5/2017 |
| JP | 2017191301 | 10/2017 |
| KR | 10-2016-0121756 | 10/2016 |
| KR | 10-2017-0009215 | 1/2017 |
| KR | 10-2017-0039930 | 4/2017 |
| KR | 20170114241 | 10/2017 |

OTHER PUBLICATIONS

Hills et al., "Assessment of Physical Activity and Energy Expenditure: An Overview of Objective Measures," Frontiers in Nutrition, Jun. 16, 2014, 1:1-16.

PCT International Search Report in International Appln. No. PCT/US2019/040956, dated Nov. 12, 2019, 15 pages.

Sawyer et al., "Walking and Running Economy : Inverse Association with Peak Oxygen Uptake," Medicine and Science in Sports and Exercise, Nov. 1, 2011, 42:1-13.

* cited by examiner

900

```
┌─────────────────────────────────────────────────────────┐
│  ESTABLISHING WIRELESS COMMUNICATION CONNECTION         │
│            WITH FITNESS MACHINE                         │
│                                                     901 │
└─────────────────────────────────────────────────────────┘
                            │
                            ▼
┌─────────────────────────────────────────────────────────┐
│              OBTAINING MACHINE DATA                     │
│                                                     902 │
└─────────────────────────────────────────────────────────┘
                            │
                            ▼
┌─────────────────────────────────────────────────────────┐
│               OBTAINING MOTION DATA                     │
│                                                     903 │
└─────────────────────────────────────────────────────────┘
                            │
                            ▼
┌─────────────────────────────────────────────────────────┐
│             OBTAINING HEART RATE DATA                   │
│                                                     904 │
└─────────────────────────────────────────────────────────┘
                            │
                            ▼
┌─────────────────────────────────────────────────────────┐
│   DETERMINING PEDOMETER OUTPUT BASED ON MOTION DATA     │
│                                                     905 │
└─────────────────────────────────────────────────────────┘
                            │
                            ▼
                           (A)
```

FIG. 9

WEARABLE COMPUTER WITH FITNESS MACHINE CONNECTIVITY FOR IMPROVED ACTIVITY MONITORING USING CALORIC EXPENDITURE MODELS

CROSS-RELATED APPLICATIONS

This application is a continuation-in-part of U.S. patent application Ser. No. 15/613,131, filed Jun. 2, 2017, for "Wearable Computer With Fitness Machine Connectivity for Improved Activity Monitoring," and also claims the benefit of priority of U.S. Provisional Patent Application No. 62/697,386, filed Jul. 12, 2018, for "Wearable Computer With Fitness Machine Connectivity for Improved Activity Monitoring Using Caloric Expenditure Models," which patent applications are each incorporated by reference herein in its entirety.

TECHNICAL FIELD

This disclosure relates generally to activity monitoring using wearable computers.

BACKGROUND

Some wearable computers (e.g., smartwatch, fitness band) include a fitness application that uses a digital pedometer to track a user's daily movements and provide custom notifications related to progress and workout results, such as distance traveled and calories burned. Some fitness applications also monitor the user's heart rate, which can be used to calculate calories burned. A typical digital pedometer relies on accelerometer data from an accelerometer to determine when a step is taken. If the wearable computer is worn on the wrist, accelerations due to arm swing are used to determine step counts. These steps counts can be inaccurate (e.g., due to irregular or muted arm swings) resulting in inaccurate distance traveled measurements. The heart rate can be measured using an optical sensor embedded in the wearable computer.

When a user works out in a gym, they will often use a fitness machine that includes a processor that monitors the workout and generates fitness metrics summarizing the workout. For example, a treadmill may display to the user the total distance traveled, elapsed time and total calories burned during the workout. The total distance traveled is typically accurate because it is based on rotation of the treadmill motor shaft rather than accelerometer data, but the total calories burned is often an estimate based on a model that does not include the actual heart rate of the user, or in the case of anaerobic calorie burn, cannot be observed through the heart rate.

SUMMARY

Embodiments are disclosed for a wireless wearable computer with fitness machine connectivity for improved activity monitoring using caloric expenditure models. In an embodiment, a method comprises: establishing, by a processor of a wireless wearable computer worn by a user, a wireless communication connection with a fitness machine; obtaining, by the processor using the communication connection, machine data from the fitness machine while the user is engaged in a workout session on the fitness machine; obtaining, from a heart rate sensor of the wireless device, heart rate data of the user; determining, by the processor, a work rate caloric expenditure by applying a work rate calorie model to the machine data; determining, by the processor, a calibrated maximal oxygen consumption of the user based on the heart rate data and the work rate caloric expenditure; determining, by the processor, a heart rate caloric expenditure by applying a heart rate calorie model to the heart rate data and the calibrated maximal oxygen consumption of the user; and sending, by the processor to the fitness machine via the communication connection, at least one of the work rate caloric expenditure or the heart rate caloric expenditure.

Other embodiments can include an apparatus, computing device and non-transitory, computer-readable storage medium.

The details of one or more implementations of the subject matter are set forth in the accompanying drawings and the description below. Other features, aspects and advantages of the subject matter will become apparent from the description, the drawings and the claims.

DETAILED DESCRIPTION

Example Operating Environment

Figure 1:
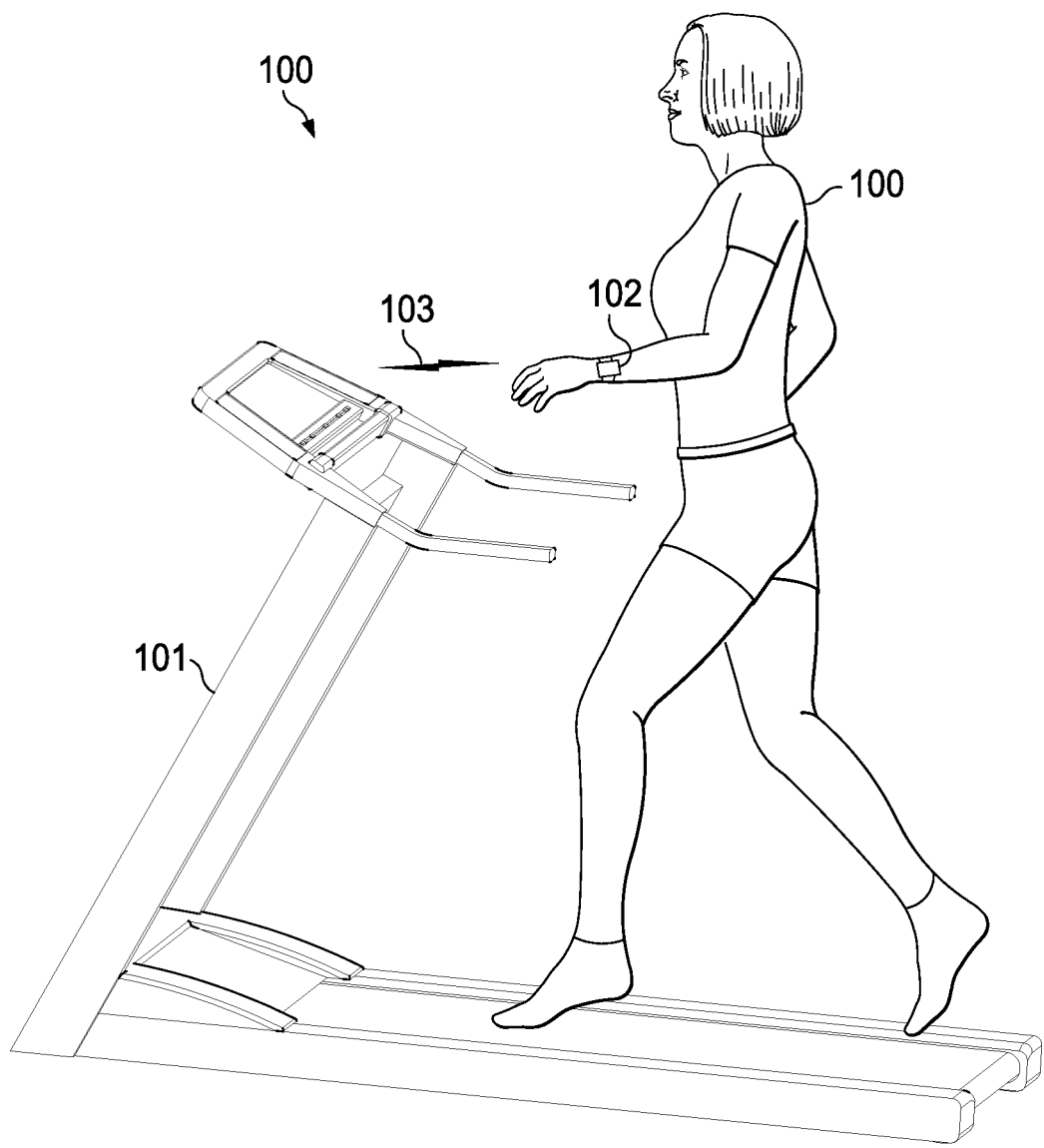
FIG. 1 illustrates an operating environment for an improved activity monitoring system that includes a wearable computer wirelessly connected to a fitness machine, according to an embodiment.

FIG. 1 illustrates an operating environment 100 for an improved activity monitoring system that includes wearable computer 102 wirelessly connected to fitness machine 101, according to an embodiment. User 100 is wearing computer 102 on her wrist while she runs on fitness machine 101, which in this example is a treadmill. Other examples of fitness machines include but are not limited to: cross-trainers (elliptical trainers), step/stair climbers, indoor bikes, indoor rowing machines and skiing machines. Wearable computer 102 can be a smart watch, fitness band, chest band, headband, earbud, activity/fitness tracker, headset, smart glasses, or any other wearable computer capable of communicating with fitness machine 101 and calculating a fitness metric. Wearable computer 102 establishes a bi-directional, wireless communication session 103 with a processor in fitness machine 101 using a wireless communication protocol. In an embodiment, session 103 can be a Bluetooth session or near field communication (NFC) session, which can be established using a "pairing" process, as described in reference to FIGS. 4 and 5. In an embodiment, fitness machine 101 is authenticated and the user's consent to share data is confirmed before bi-directional data sharing is allowed between wearable computer 102 and fitness machine 101.

Wearable computer 102 includes a processor and memory that includes instructions for running a fitness application that can be executed by the processor. The fitness application runs on wearable computer 102 during the user's workout session on fitness machine 101. A processor in fitness machine 101 monitors the workout session and computes various data (hereinafter referred to as "machine data") related to the workout session, including but not limited to: total energy used, total distance run, elapsed time, instantaneous speed, average speed, inclination and positive elevation gain. The machine data is transferred over link 103 to computer 102 where it is used by the fitness application, together with data known to computer 102 (hereinafter referred to as "wearable computer data,") to calculate one or more fitness metrics, such as calories burned. As described in further detail below, wearable computer 102 can include a heart rate monitor for determining the user's heart rate, which can be combined with machine data to determine calories burned.

During the workout session, one or more fitness metrics calculated by wearable computer 102 are transferred back to fitness machine 101 where the metrics are displayed on a monitor of fitness machine 101. During the workout session and/or after the workout session ends, a workout summary including the fitness metrics is transferred to computer 102. The user can view the details of the workout session at any time on fitness machine 101, or on wearable computer 102. In an embodiment, wearable computer 102 displays an in-session view with metrics received from fitness machine 101, as well as heart rate and calories (total/active) computed by wearable computer 102. The user can use computer 102 to transfer the workout summary to another device by syncing directly with the other device or indirectly through a network (e.g., the Internet). In an embodiment, the workout session summary can be shared with other user devices in the gym through a wireless local area network (WLAN) or a multi-peer ad hoc mesh network. In this manner, users can compare their fitness metrics with friends, trainers and other individuals for a particular fitness machine while in the gym. In an embodiment, and with the consent of users, anonymous summary data can be processed by a server computer to provide workout statistics for a particular fitness machine over a large sample set. Such statistics can be used by gym operators, fitness machine manufacturers and other interested entities to determine what machines are most popular, the average time spent on a machine and other useful information.

In addition to calculating fitness metrics, wearable computer 102 can use machine data to calibrate a digital pedometer running on wearable computer 102. For example, the total distance traveled during a workout session computed by fitness machine 101 can be used with an estimated distance traveled during the workout session based on pedometer step count to determine a calibration factor (e.g., a ratio of the two numbers). The calibration factor can be used to scale the estimated distance traveled calculated by computer 102 to correct out the error in the estimate.

Example System

Figure 2:
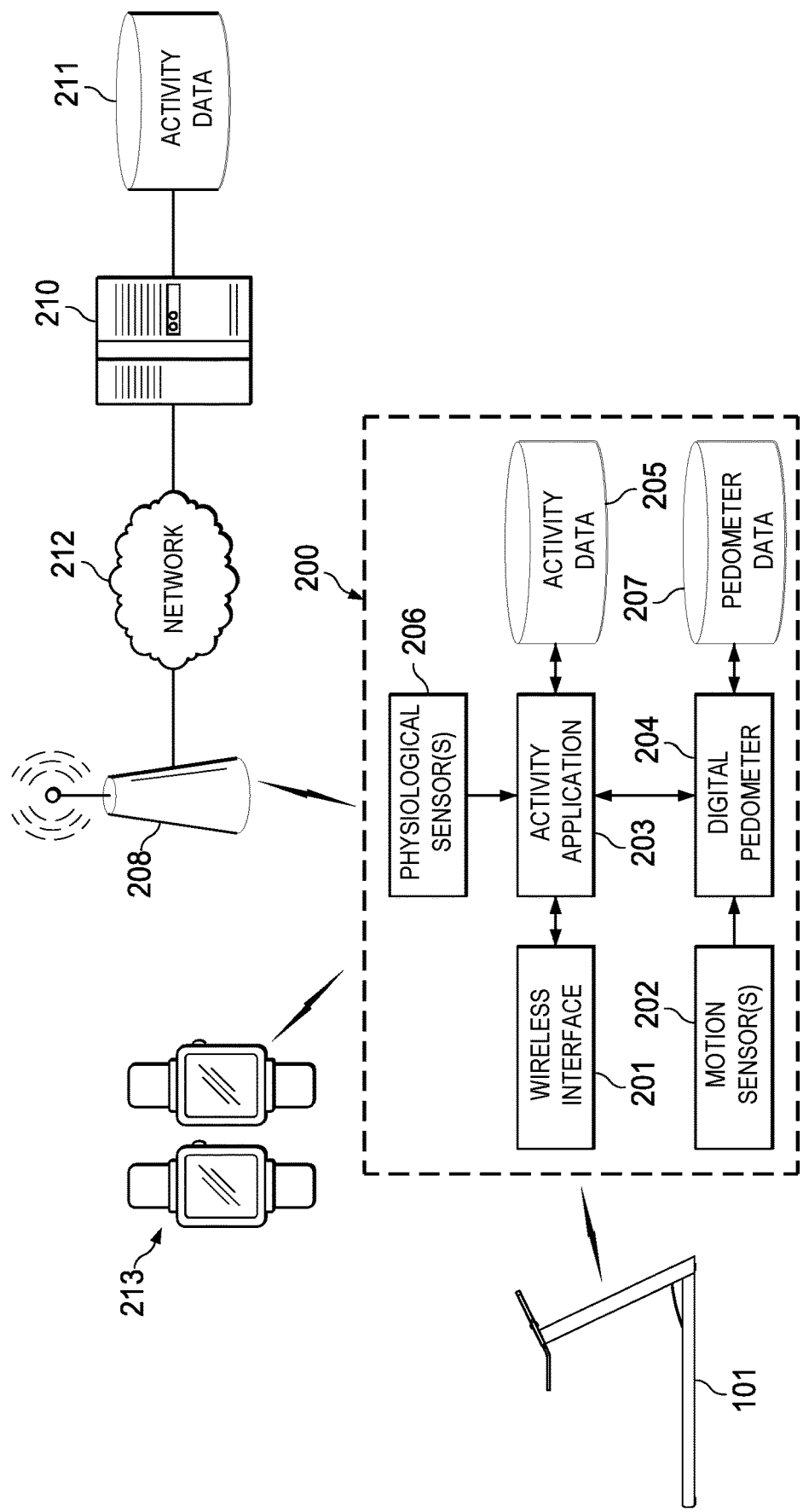
FIG. 2 is a block diagram of an example activity monitoring system for improved activity monitoring using wearable computer data combined with fitness machine data, according to an embodiment.

FIG. 2 is a block diagram of an example activity monitoring system for improved activity monitoring using wearable computer data combined with fitness machine data, according to an embodiment. System 200 can be implemented in wearable computer 102, such as a smartwatch or fitness band. System 200 includes wireless interface 201, motion sensor(s) 202 (e.g., accelerometers, gyros, magnetometer), fitness application 203, digital pedometer 204, activity data 205, physiological sensor(s) 206 and pedometer data 207. System 200 can be wired or wirelessly coupled to network 212 through WLAN access point 208 (e.g., a Wi-Fi router) to transfer data and/or sync with activity data 211 through network server computers 210.

In an embodiment, wireless interface 201 includes a wireless transceiver and other hardware (e.g., an antenna) and software (e.g., a software communication stack) for establishing, maintaining and ending a wireless communication session with fitness machine 101, as described in reference to FIG. 1. In an embodiment, wireless interface 201 can also be configured to establish, maintain and end a wireless communication session with WLAN access point 208, and/or other devices 213 through a multi-peer ad hoc mesh network.

In an embodiment, motion sensors, such as accelerometers provide acceleration data that can be used by digital pedometer 204 to determine step count and calculate an estimated distance traveled based on the step count and a stride length of the user. The stride length can be based on an average stride length for the user given the gender and height of the user, or it can be determined automatically based on sensor data. Pedometer data 207 including step count and distance traveled can be stored on wearable computer 102 (e.g., stored in flash memory).

Fitness application 203 can be a software program that is executed by one or more processors of wearable computer 102. Fitness application 203 use pedometer data 207 to track a user's daily movements and provide customize notifications related to progress and workout results, such as distance traveled and calories burned. Fitness application 203 also monitors the user's heart rate and other physiology of the user, which can be calculated from sensor data provided by physiological sensor(s) 206. Some examples of physiological sensors 206 include but are not limited to: heart rate (pulse) sensors, blood pressure sensors, skin temperature and/or conductance response sensors and respiratory rate sensors. In an embodiment, physiological sensor(s) 206 include a heart rate sensor comprising a number of light emitting diodes (LEDs) paired with photodiodes that can sense light. The LEDs emit light toward a user's body part (e.g., the user's wrist), and the photodiodes measure the reflected light. The difference between the sourced and reflected light is the amount of light absorbed by the user's body. Accordingly, the user's heart beat modulates the reflected light, which can be processed to determine the user's heart rate. The measured heart rate can be averaged over time to determine an average heart rate.

A heart rate monitor (FIRM) does not measure caloric expenditure. Rather, the HRM estimates caloric expenditure during steady-state cardiovascular exercise using a relationship between heart rate and oxygen uptake ($VO_2$). A commonly accepted method for measuring the calories burned for a particular activity is to measure oxygen uptake ($VO_2$). During steady-state aerobic exercise, oxygen is utilized at a relatively consistent rate depending on the intensity of the exercise. There is an observable and reproducible relationship between heart rate and oxygen uptake. When workload intensity increases, heart rate increases and vice versa. If the user's resting heart rate, maximum heart rate, maximum oxygen uptake and weight are known, caloric expenditure can be estimated based on a percentage of their maximum heart rate or a percentage of their heart rate reserve.

The metabolic equivalent of tasks (MET) is the ratio of the rate of energy expended during a specific physical activity to the rate of energy expended at rest. By convention, the resting metabolic rate (RMR) is 3.5 ml $O_2 \cdot kg^{-1} \cdot min^{-1}$, and 1 MET is defined by Equation 1:

$$1 \, MET = 1 \frac{kcal}{kg*h} = 4.184 \frac{kJ}{kg*h} = 1.162 \frac{W}{kg}. \quad [1]$$

Using Equation [1], a 3 MET activity expends 3 times the energy used by the body at rest. If a person does a 3 MET activity for 30 minutes she has done 3×30=90 MET-minutes of physical activity. Since the rate of energy expenditure is dependent on the intensity of the physical activity, it follows that the energy expenditure is also dependent on the type of fitness machine used in the workout session. For example, a vigorous jog on a treadmill may have a MET greater than 6 and a light workout on a stationary indoor bike may have a MET of 3 or less.

In an embodiment, a look-up table of MET values can be stored as activity data 211. During a workout session, fitness machine 101 sends machine data includes the fitness machine type that can be used by fitness application 203 to identify the physical activity and select a suitable MET for the physical activity. For example, if the fitness machine type indicates a treadmill, then a MET that is suitable for jogging on a treadmill can be selected for calculation of calories expended C using Equation [2]:

$$C = MET \times time \, (minutes) \times weight \, (kg), \quad [2]$$

where MET is the MET associated with a particular fitness activity and can be retrieved from, for example, a look-up table stored by wearable computer 102.

Published MET values and values used by fitness machines for specific physical activities are often averages that are experimentally or statistically derived from a sample of people. The level of intensity at which the user performs a specific physical activity (e.g., walking pace, running speed) will deviate from the average MET values. To personalize caloric expenditure to the user, a more accurate model can be used on wearable computer 102 to calculate caloric expenditure, as described in reference to FIGS. 8 and 9.

Example Use Cases

Figure 3:
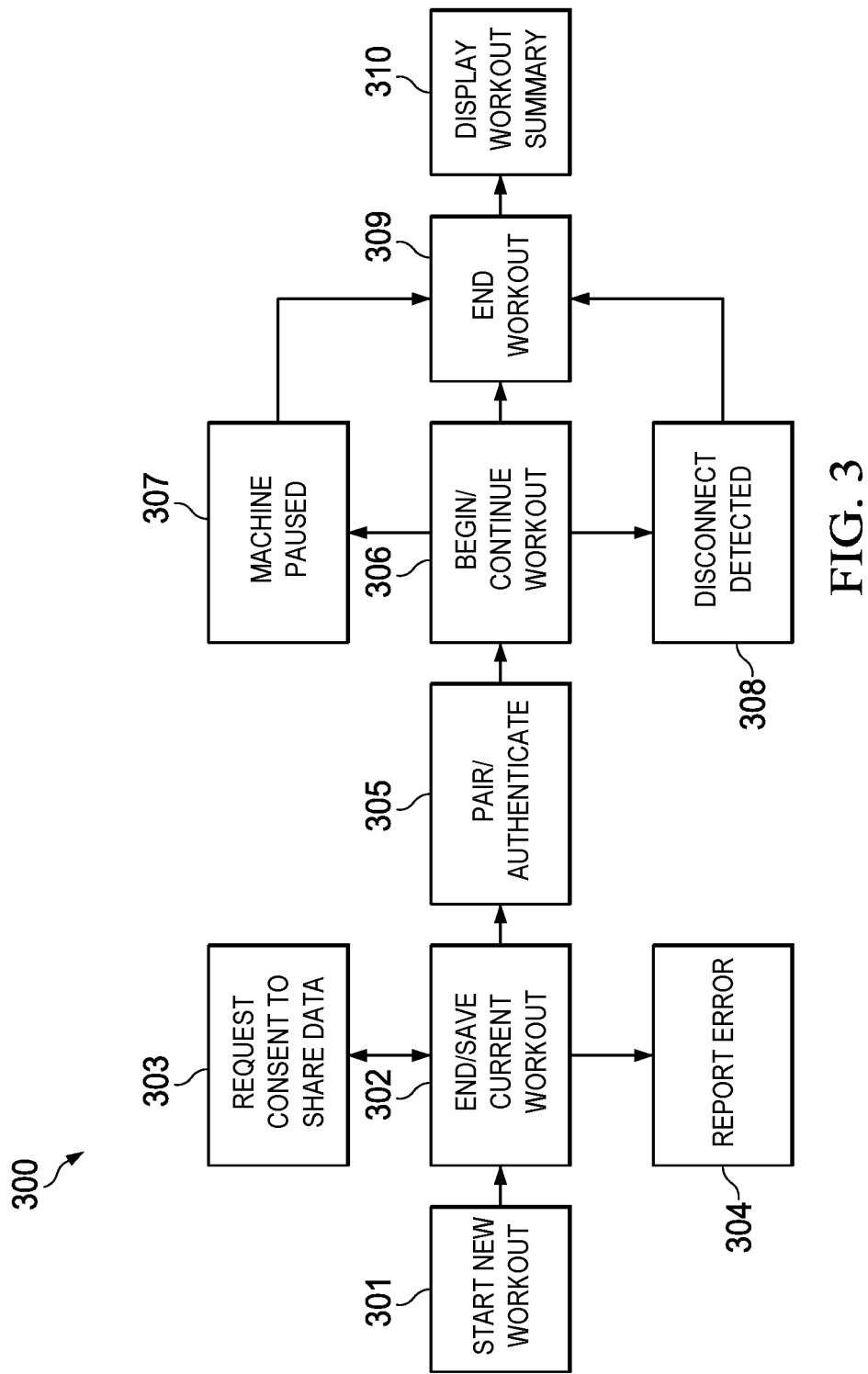
FIG. 3 is an example process flow for connecting a wearable computer with a fitness machine, according to an embodiment.

FIG. 3 is an example process flow 300 for connecting a wearable computer with a fitness machine, according to an embodiment. There are four use cases for connecting a wearable computer with a fitness machine: 1) the user pairs first with the fitness machine, then starts their workout, 2) the user starts their workout with the wearable computer and then pairs with the fitness machine, 3) the user starts their workout with the fitness machine and then pairs with the wearable computer, and 4) the user has simultaneous workouts on the wearable computer and the fitness machine. Each use case will be described in turn.

In the first use case, the user visits the gym and finds a fitness machine with a badge (e.g., an RFID tag) indicating the machine can be paired to a wearable computer, which in this example is a smartwatch strapped to the user's wrist. The user starts a new workout session (301) by placing their wearable computer near the badge to begin pairing. When the wearable computer is near the badge (e.g., less 10 cm) its proximity to the badge is detected using, for example, magnetic induction between loop antennas located in the wearable computer and the badge.

If it is the user's first time pairing with the fitness machine, the user is requested to consent to share data (303) with the fitness machine. The request for consent can be in the form of a GUI affordance presented on a display of the wearable computer. If the user has already consented (e.g., based on a previous connection with the fitness machine), the user will be requested to pair with the fitness machine. Since, in this first use case, the user is not in a current workout session, step 302 is not applicable. If the user agrees to pair, a pairing/authentication process begins (305). If an error occurs during the pairing/authentication the error is reported to the user (304). An error can be due to a connection failure and/or an authentication failure.

Since personal physiological data is being transferred to a public fitness machine, the wearable computer and fitness machine perform an authentication procedure before sharing of the user's personal fitness data is allowed. During the authentication process, and in an embodiment that uses public-private key encryption, the fitness machine generates and securely stores a public key-private key pair, which can be in the format of elliptical curve digital signature algorithm (ECDSA) or any other suitable digital signature algorithm. The fitness machine then calculates a message digest (e.g., a SHA256 message digest) using the private key and other data. The other data can be, for example, a random number, a connection confirmation value, local name data, etc. The fitness machine then uses the encoded public key and message digest to perform the authentication process. Upon successful authentication of the fitness machine, the wearable computer and fitness machine begin pairing.

After successful pairing, the user begins the physical workout on the fitness machine (306) by, for example, starting the machine (e.g., starting the treadmill). During the workout session, the wearable computer displays an affordance indicating that the wearable computer and fitness machine are paired and the workout session is active. During an active workout session all of the current metrics are displayed by the wearable computer. If the fitness machine is paused, the workout session on the wearable computer is also paused, and the wearable computer displays a GUI stating that the workout on the wearable computer cannot pause. If the pause is extended (307) (e.g., more than 1.5 minutes), the workout session ends (309) and a workout session summary is displayed to the user (310). If the wearable computer becomes disconnected from the fitness machine during the workout session, the wearable computer reports to the user that it has disconnected from the fitness machine. If the disconnect is extended (308) (e.g., more than 1.5 minutes), the workout session ends (309) and a workout session summary is displayed to the user (310). In an embodiment, a GUI affordance is displayed by the wearable computer that allows the user to disconnect and end the active workout session on the wearable computer without effecting the workout on the fitness machine.

In the second use case, the user is already in a workout session on their wearable computer. For example, the user may have entered the gym after an outdoor run with a workout session running on their wearable computer. In this second use case, the user starts a new workout session (301) by placing the wearable computer near the badge on the fitness machine. In an embodiment, if the user already consented to share data, the user is prompted with an affordance to end and save the current workout session and begin pairing with the fitness machine. If the user agrees, the current workout session is terminated and saved (302) and the pairing/authentication process begins (305). If the user does not agree, the pairing/authentication is not performed and the current workout session remains active on the wearable computer. In an embodiment, the current workout session is automatically terminated and saved by the wearable computer, and a pairing screen is displayed on the wearable computer.

After a successful pairing/authentication process, the user begins the physical workout (306). When the new workout session ends (309) (including by extended pause 307 or extended disconnect 308), data from both the previous and current workout sessions are displayed in a workout session summary (310).

In an embodiment, if the user did not consent to share data, the user is prompted with a GUI affordance requesting the user's consent to share data (303), end and save their current workout session and begin the pairing/authentication process. If the user consents to share data, the current workout session is terminated and saved (302) and the pairing/authentication process begins (305). If the user does not consent to share data, the pairing/authentication process ends and the current workout session remains active on the wearable computer. In an embodiment, the current workout session is automatically terminated and saved by the wearable computer, and a pairing screen is displayed on the wearable computer.

In the third use case, the user starts a new workout session (301) on the fitness machine but not the wearable computer. During the workout session, the user notices the badge and places their wearable computer near the badge. If the user already consented to share data, the user is prompted to pair. If the user agrees to pair, the pairing/authentication process begins (305). If the pairing/authentication process is successful, the wearable computer and fitness machine are paired. The user can continue their physical workout on the fitness machine (306). The fitness data accrued by the user on the fitness machine is ingested into the wearable computer so that the user does not lose any data, even though they may have started the workout session on the wearable computer after they started the workout session on the fitness machine. When the workout session ends (309) (including by extended pause 307 or extended disconnect 308), a summary of the workout session is displayed (310).

If the user did not previously consent to share data, the user is requested to consent (303). If the user consents, pairing begins (305). If the pairing/authentication process is successful, the wearable computer and fitness machine are paired. The user continues the physical workout on the fitness machine (306). When the workout session ends (309) (including by extended pause 307 or extended disconnect 308) a summary of the workout session is displayed (310). If the user does not consent to share data, pairing/authentication is not performed and the user can continue with the physical workout on the fitness machine without the wearable computer running a workout session.

In the fourth use case, the user is simultaneously engaged in a fitness machine workout and a wearable computer workout. The user starts a new workout (301) by placing their wearable computer near a badge on the fitness machine. In an embodiment, if the user has already consented to share data, the user is prompted to end and save their current workout and begin pairing. If the user agrees, the current workout is terminated and saved (302) and pairing/authentication begins (305). If the user does not agree, the pairing/authentication process is not performed. In an embodiment, the current workout session is automatically terminated and saved by the wearable computer, and a pairing screen is displayed on the wearable computer. If the pairing/authentication process is successful, the wearable computer and fitness machine are paired. When the new workout session ends (309) (including by extended pause 307 or extended disconnect 308), both the summary of the previously saved workout session and the new workout session are displayed (310).

If the user has not consented to share data, the user is requested to end and save the current workout session (302) and consent to sharing data (303), if the user agrees, the current workout session ends, a summary of the workout session is saved and pairing begins (305). If the pairing/authentication process is successful, the user begins the new workout (306). When the new workout session ends (309) (including by extended pause 307 or extended disconnect 308), a summary of the saved workout session and the new workout session are displayed (310).

Figure 4:
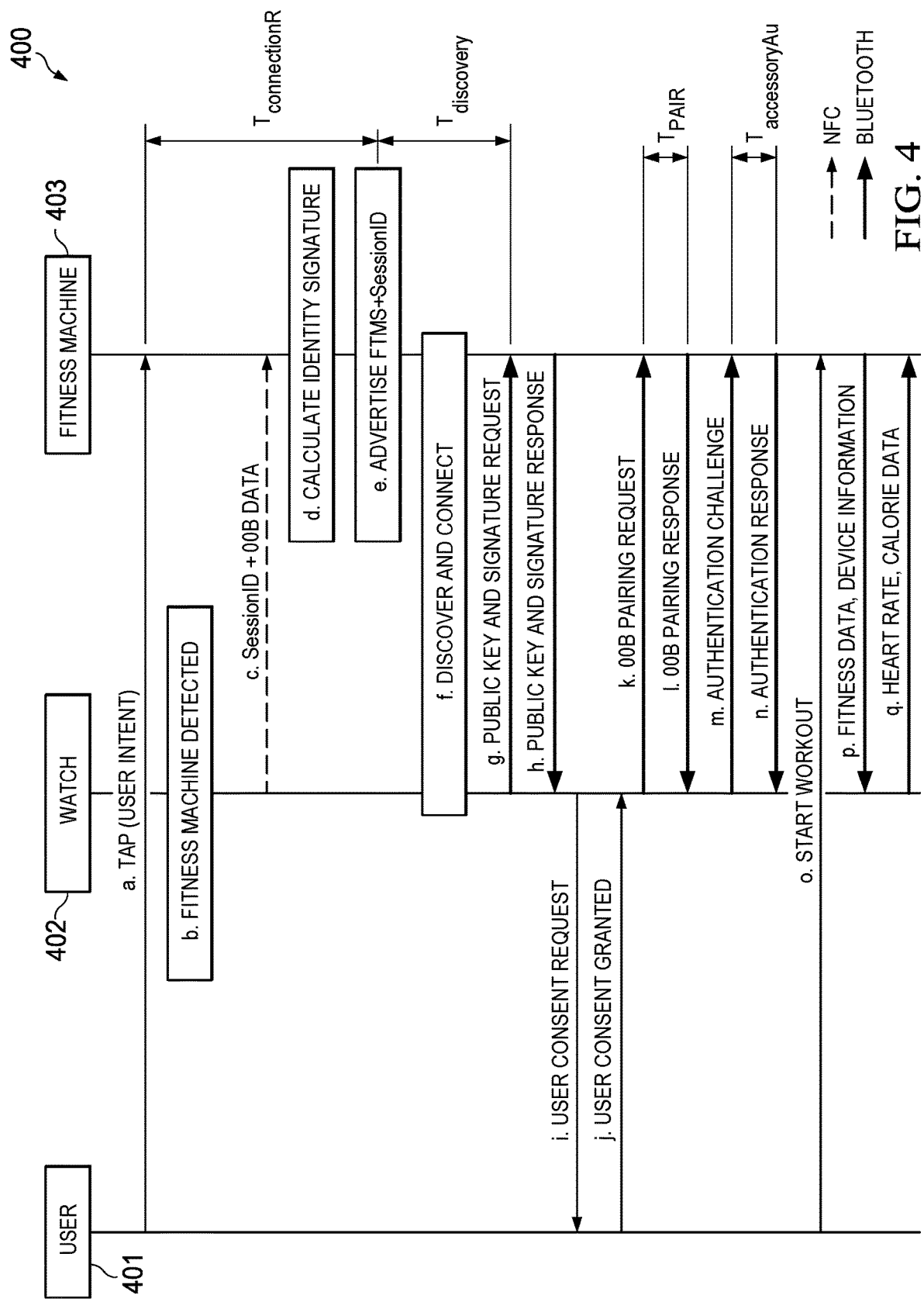
FIG. 4 is a swim lane diagram of example connection establishment procedures, according to an embodiment.

FIG. 4 is a swim lane diagram illustrating example connection establishment procedures using NFC, according to an embodiment. In the diagram there are three actors including user 401, wearable computer 402 and fitness machine 403. Each step in the diagram is indicated by a letter, starting with the letter "a" and ending with the letter "q".

The connection establishment procedures begin when user 401 signals to fitness machine 403 their intent to pair with fitness machine 403 (step "a") by placing the wearable computer near the badge on the fitness machine.

During a timed connecting interval $T_{connectionReady}$, fitness machine 403 is detected by wearable computer 402 (step "b"), wearable computer 402 sends a SessionID (e.g., a unique number per pairing attempt) and out-of-band (OOB) secret data (unique per connection) to fitness machine 403 (step "c") and fitness machine 403 calculates an identify digital signature (step "d") using for example, ECDSA. In an embodiment, the OOB secret data can comply with Security Manager Specification of Bluetooth Core Specification, Volume 3, Part H. Fitness machine 403 can include an NFC reader for reading the SessionID and OOB secret data.

During a timed discovery interval $T_{discovery}$, fitness machine 403 advertises a fitness machine service (FTMS) and the Session ID (step "e"). Wearable computer 402 discovers fitness machine 403 via the advertisement (step "f") and provides a public key and signature request (step "g").

Fitness machine 403 sends to wearable computer 402 the public key and a signature response (step "h"). Wearable computer 402 sends a consent request to user 401 (step "i"), user 401 grants the request (step "j").

During a timed pairing interval $T_{pair}$, wearable computer 402 sends an OOB pairing request (step "k") to fitness machine 403 and fitness machine 403 sends an OOB pairing response to wearable computer 402 (step "l").

During a timed authentication interval $T_{accessoryAuth}$, wearable computer 402 sends an authentication challenge to fitness machine 403 (step "m") and receives an authentication response from fitness machine 403 (step "n").

Upon successful authentication, user 401 starts the workout (step "o"), machine data (e.g., fitness machine type, total energy used, elapsed time, total distance) is sent to wearable computer 402 (step "p") and fitness data (e.g., instantaneous and average heart rate, active and total calories) is sent from wearable computer 402 to fitness machine 403 (step "q"). The data is communicated using, for example, NFC or Bluetooth standard protocols (e.g., Bluetooth Core Specification version 4.2, NFC Suite B version 1.0).

Figure 5:
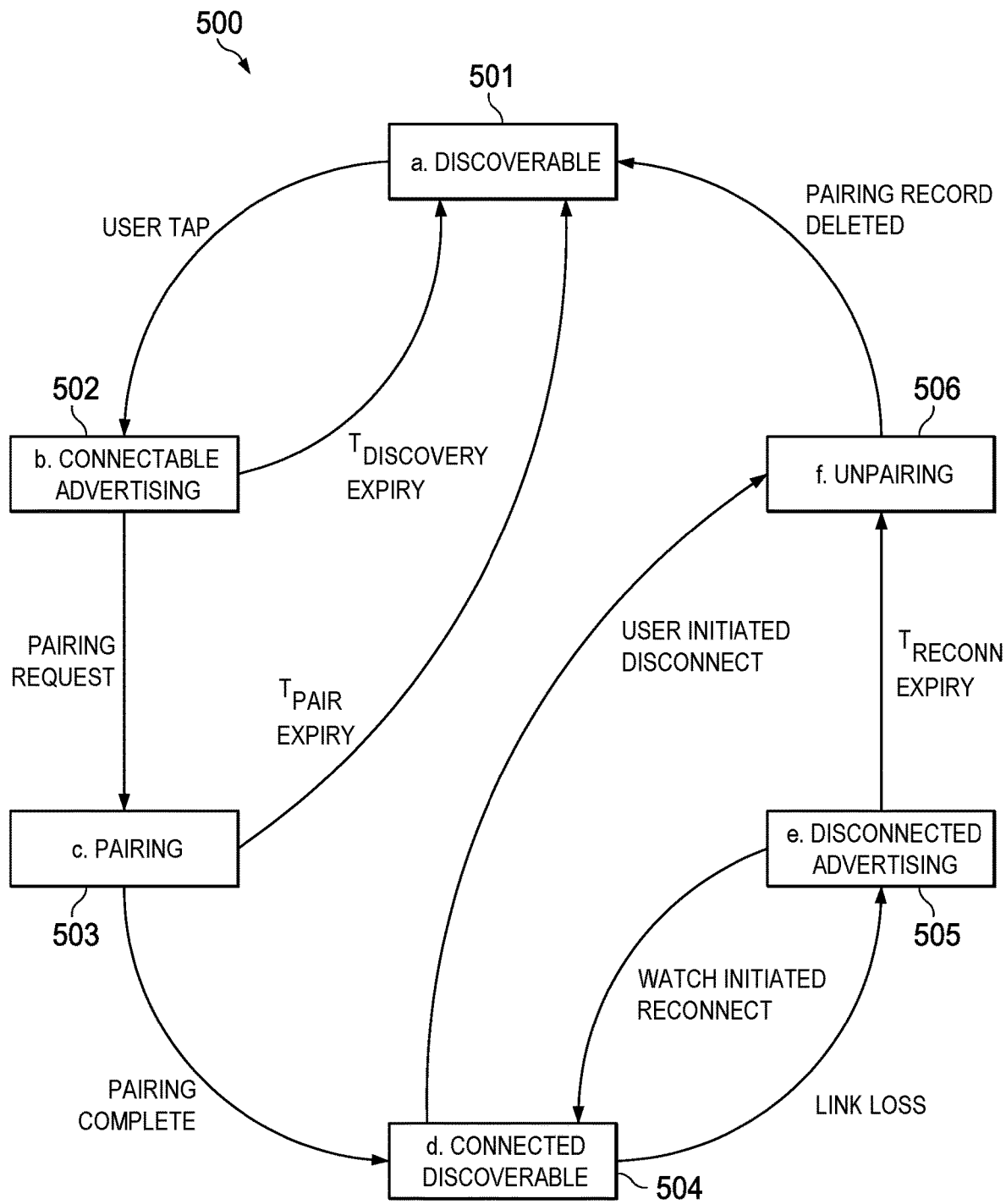
FIG. 5 is a state diagram illustrating an example state machine implemented by a fitness machine processor for connecting and establishing a session with a wearable computer, according to an embodiment.

FIG. 5 is a diagram illustrating an example state machine 500 implemented by a fitness machine processor for connecting and establishing a session with a wearable computer, according to an embodiment. Each state is indicated by a letter, starting from "a" and ending with "f".

The fitness machine starts in a discovery state 501 (state "a") where the fitness machine is idle and its NFC reader is ready to rea a user's tag. When a user intent to connect is detected ("tap"), state 501 transitions to connectable advertising state 502 (state "b") and the fitness machine advertises at a timed interval $T_{connectionAdv}$. Included in the advertising packet is the SessionID and FTMS. When a pairing request is received from a wearable computer, state 502 transitions to pairing state 503 (state "c"). In state 503, the fitness machine responds to an identity verification request, authentication challenge and pairing request.

When pairing is complete, state 503 transitions to connected discoverable state 504 (state "d"), where the fitness machine is paired to the wearable computer. If the link is lost, connected discoverable state 504 transitions to a disconnected advertising state 505 (step "e"). In state 505, the fitness machine is no longer able to communicate with the wearable computer and starts advertising as non-discoverable to facilitate reconnection. When a reconnect time $T_{reconnect}$ expires, disconnected advertising state 505 transitions to unpairing state 506 (step "f"). In state 506, the fitness machine deletes its current pairing record.

If the fitness machine is in the connected discoverable state 504, and the user initiates disconnect, the connected discoverable 504 transitions to the unpairing state 506. If the fitness machine is in the disconnected advertising state 505, and the wearable computer initiates a reconnect, the disconnected advertising state 505 transitions to the disconnected discoverable state 504. If the fitness machine is in the pairing state 503, and a pairing time $T_{pair}$ expires, the pairing state 503 transitions to the discoverable state 501. If the fitness machine is in the connectable advertising state 502, and a discovery time $T_{discovery}$ expires, the connectable advertising state 502 transitions to the discoverable state 501.

In an embodiment, the user may determine how pairing will operate on their wearable computer. The user can select various pairing options using one or more GUI affordances or hardware input mechanisms. For example, a switch can allow the user to turn auto pairing on and off. Auto pairing is where the user does not have to say yes to pair if they have accepted pairing with a fitness machine in the past. Another switch allows the user to select automatic pairing to be always turned on or turned on only when the user has launched the fitness application on the wearable computer. If automatic pairing is only allowed when the workout application is launched, the user will have to launch the workout application to pair with a fitness machine. In an embodiment, if the wearable computer determines that the user has completed at least one workout session on the wearable computer, then automatic pairing remains turned on regardless of whether or not the fitness application is launched. If the user has not completed a workout session, the user will need to launch the fitness application to turn on automatic pairing.

In an embodiment, a GUI affordance or hardware input mechanism can be used to clear a particular fitness machine, or all fitness machines, listed in a pairing record stored on the wearable computer. If, however, the wearable computer was paired with a particular fitness machine in the past, and the user attempts to pair within x days (e.g., 90 days) from the last pairing, the wearable computer will auto-connect with the fitness machine. Otherwise, the user will be prompted to perform a pairing/authentication process with the fitness machine, as described in reference to FIGS. 3-5.

Figure 6:
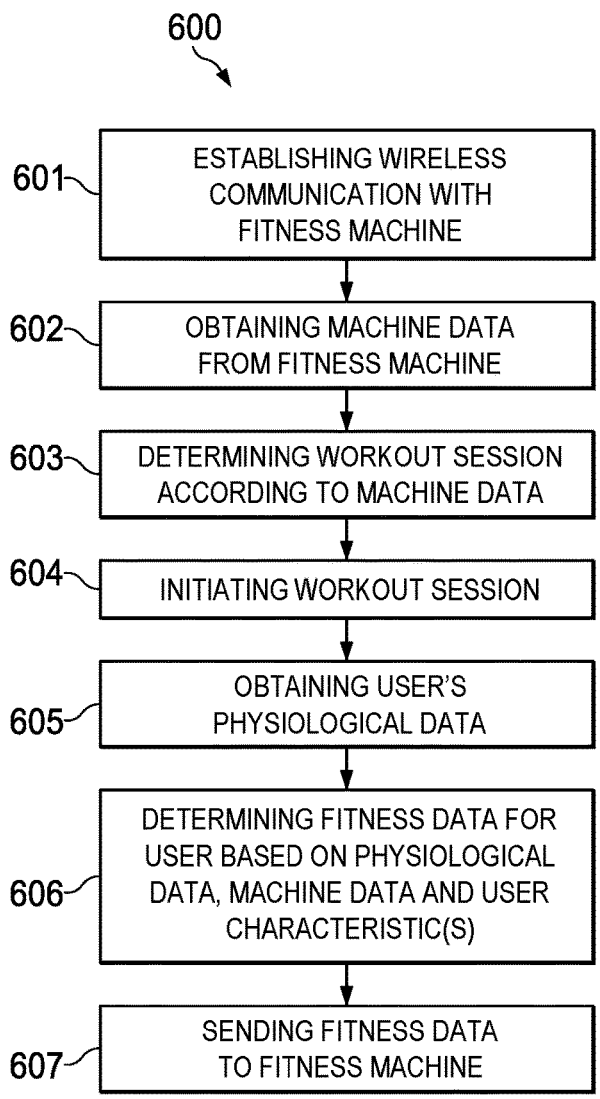
FIG. 6 is a flow diagram of an example process performed by a wearable computer for calculating fitness data, according to an embodiment.

FIG. 6 is a flow diagram of an example process performed by a wearable computer for calculating fitness data, according to an embodiment. Process 600 can be implemented by architecture 600, as described in reference to FIG. 8.

Process 600 can begin by establishing wireless communication with a fitness machine (601). For example, a Bluetooth or NFC session can be established with the fitness machine, as described in reference to FIGS. 3-5. A unique SessionID and OOB secret data can be calculated on the wearable computer and sent to the fitness machine for use in pairing and authentication.

Process 600 continues after pairing by obtaining machine data from the fitness machine (602). After successful pairing and authentication, machine data can be transferred to the wearable computer using Bluetooth or NFC session data packets. The machine data can include, for example, data that describes the fitness machine, including but not limited to: manufacturer name, model number, hardware revision, software revision, vendor ID, product ID. Additionally, various fitness metrics can be included in the machine data, such as total energy, total distance and elapsed time. Some fitness metrics for different types of fitness machines is described in Table I below.

TABLE I

Fitness Machine Metrics

| Fitness Machine | Metric | Units | Resolution |
| --- | --- | --- | --- |
| Treadmill | Total Energy | kilo calories | 1 kilo calorie |
| | Total Distance | meters | 1 meter |
| | Elapsed Time | seconds | 1 second |
| | Instantaneous Speed | kilometers per hour | 0.01 kilometer per hour |
| | Average Speed | kilometers per hour | 0.01 kilometer per hour |

TABLE I-continued

Fitness Machine Metrics

| Fitness Machine | Metric | Units | Resolution |
|---|---|---|---|
| | Inclination | percent grade | 0.1 percent grade |
| | Positive Elevation Gain | meters | 0.1 meters |
| Cross Trainer | Total Energy | kilo calories | 1 kilo calories |
| | Total Distance | meters | 1 meter |
| | Elapsed Time | seconds | 1 second |
| | Positive Elevation Gain | meters | 1 meter |
| | Stride Count | — | 1 |
| | Resistance Level | — | 1 |
| | Instantaneous Power | watts | 1 watt |
| Step/Stair Climber | Total Energy | kilo calories | 1 kilo calorie |
| | Elapsed Time | seconds | 1 second |
| | Positive Elevation Gain | meters | 1 meter |
| | Floors | — | 1 |
| | Stride/Step Count | — | 1 |
| Indoor/Stationary Bike | Total Energy | kilo calories | 1 kilo calorie |
| | Total Distance | meters | 1 meter |
| | Elapsed Time | seconds | 1 second |
| | Instantaneous Cadence | — | 0.5 |
| | Average Cadence | — | 0.5 |
| | Resistance Level | — | 1 |
| | Instantaneous Power | watts | 1 watt |
| | Average Power | watts | 1 watt |
| Rowing Machine | Total Energy | kilo calories | 1 kilo calorie |
| | Total Distance | meters | 1 meter |
| | Elapsed Time | seconds | 1 second |
| | Stroke Count | — | 1 |
| | Resistance Level | — | 1 |
| | Instantaneous Power | watts | 1 watt |

Process 600 continues by determining a workout session according to the machine data (603). Based on the machine data, the wearable computer learns the specific physical activity the user will be engaged in during the workout session. For example, if the fitness machine is a treadmill then the wearable computer will know what fitness metrics may be received from the fitness machine and how to calculate fitness data for the workout. This can include adjusting parameters of a calorie model, such as, for example, determining an appropriate MET for calculating calorie expenditure.

Process 600 continues by initiating a workout session (604). For example, the user starts the fitness machine. Process 600 continues by obtaining, during the workout, the user's physiological data (605). The physiological data can be any data that measures the physiology of the user during the workout, including but not limited to: heart rate sensors, pulse detectors, blood pressure sensors, skin temperature and/or conductance response sensors, respiratory rate sensors, etc. The sensors can be included in any suitable housing, including but not limited to: a smartwatch or watchband, fitness band, chest band, headband, finger clip, ear clip, earbud, strapless heart rate monitor, etc.

Process 600 continues by determining fitness data, during the workout session, for the user based on the physiological data, machine data and user characteristic(s) (606). For example, calories burned can be calculated using knowledge of the physical activity, the total energy, total distance, elapsed time any other data shown in Table I that can be used in a calorie expenditure model. Any suitable calorie expenditure model can be used, including models that are dependent on MET and not dependent MET, and models that include any type and combination of user characteristics, such as height, weight, age and gender.

Process 600 continues by sending the fitness data, during the workout session, to the fitness machine (607). After calculating the fitness data, the wearable computer sends the fitness data to the fitness machine where it can be displayed on a monitor of the fitness machine. In an embodiment, the fitness data is also stored on the wearable computer. The stored fitness data can be synced to another device including a network-based server computer and shared with other devices through a client-server architecture. In an embodiment, the fitness data can be shared directly with other devices (e.g., devices owned by friends, trainers, etc.) in a multi-peer ad hoc mesh network.

Figure 7:
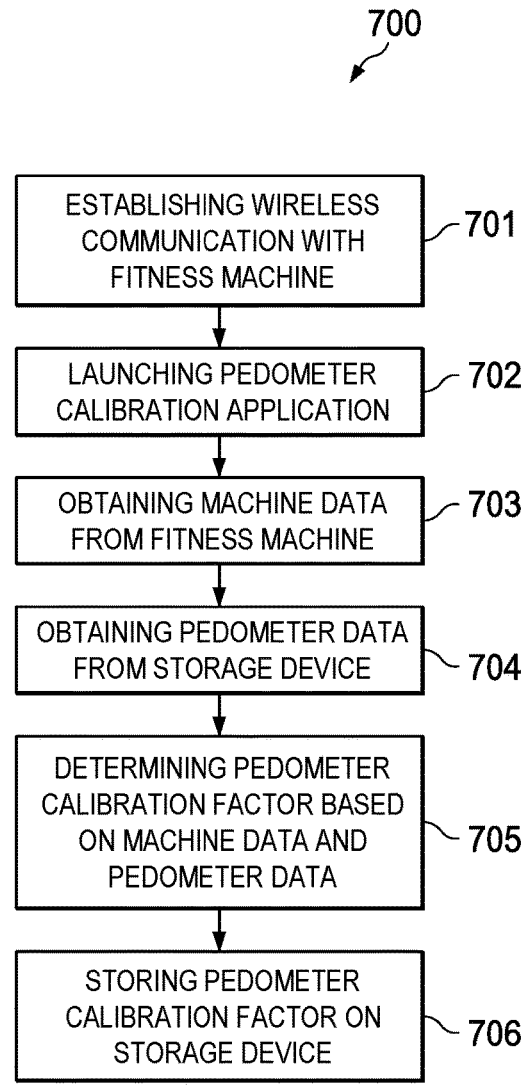
FIG. 7 is a flow diagram of an example process performed by a wearable computer to calibrate a digital pedometer, according to an embodiment.

FIG. 7 is a flow diagram of an example process 700 performed by a wearable computer to calibrate a digital pedometer, according to an embodiment. Process 700 can be implemented by architecture 700, as described in reference to FIG. 8.

Process 700 begins by establishing wireless communication with a fitness machine (701). For example, a Bluetooth or NFC session can be established with the fitness machine, as described in reference to FIGS. 4 and 5.

Process 700 continues by launching a pedometer calibration application on the wearable computer (702). The pedometer application can measure step counts based on sensor data, such as accelerometer data provided by an accelerometer on the wearable computer.

Process 700 continues by obtaining machine data from the fitness machine (703). After a successful pairing/authentication process, the fitness machine can send data to the wearable computer that indicates the specific physical activity engaged in by the user during the workout. Additionally, the machine data can include information that can be used to calibrate the digital pedometer, such as total distance data from a treadmill.

Process 700 continues by obtaining pedometer data (704). Pedometer data can include step count or distance traveled which can be calculated from the step count and the user's stride length.

Process 700 continues by determining a pedometer calibration factor based on the machine data and the pedometer data (705). For example, a ratio can be formed from the total distance provided in the machine data over the estimated distance provided by the digital pedometer. The ratio can be used as a calibration scale factor to correct future pedometer measurements by scaling the estimated distance by the ratio. Process 700 continues by storing the calibration factor (706). The calibration can be performed each time the user uses a treadmill.

Example Calorie Expenditure Models that Use Fitness Machine Data

An effective and accurate way of calculating caloric expenditure for a user is through the use of oxygen uptake $VO_2$. $VO_2$ is a good indicator of exercise intensity because it is tied closely to energy expenditure. The higher the intensity, the more oxygen a user consumes and the more calories the user burns. American College of Sports Medicine (ACSM) provides $VO_2$ models that can be used to predict caloric expenditure for various types of fitness machines (e.g., treadmill, rower, stair climber, indoor bike, elliptical). For example, for walking, $VO_2=(0.1\times speed)+(1.8\times speed\times grade)+3.5$. This equation is appropriate for fairly slow speed ranges—from 1.9 to approximately 4 miles per hour (mph). Speed is calculated in meters per minute (m/min). The numbers 0.1 and 1.8 are constants that refer to the following: 0.1=oxygen cost per meter of moving each kilogram (kg) of body weight while walking (horizontally) and 1.8=oxygen cost per meter of moving total body mass against gravity (vertically). For running, the $VO_2=(0.2\times speed)+(0.9\times speed\times grade)+3.5$. This equation is appropriate for speeds greater than 5.0 mph (or 3.0 mph or greater if the subject is truly jogging). Speed is calculated in m/min. The constants refer to the following: 0.2=oxygen cost per meter of moving each kg of body weight while running (horizontally) and 0.9=oxygen cost per meter of moving total body mass against gravity (vertically). These ACSM models, however, are often inaccurate because they were developed using a few adult men of average height. The wearable computer described herein can provide more accurate caloric expenditure calculations by using fitness machine data, such as speed and grade data provided by a treadmill machine, and then applying new models to the fitness machine data to calculate more accurate caloric expenditure for the fitness machine user.

In the description that follows, calorimetry modeling is used to improve work rate (WR) calorie estimates based on fitness machine input for parameters, such as speed, elevation, etc. calorimetry modeling also improves the estimation of $VO_2$ max by calibrating $VO_2$ max when a user is in a fitness machine workout session.

Example Data Flows

Figure 8A:
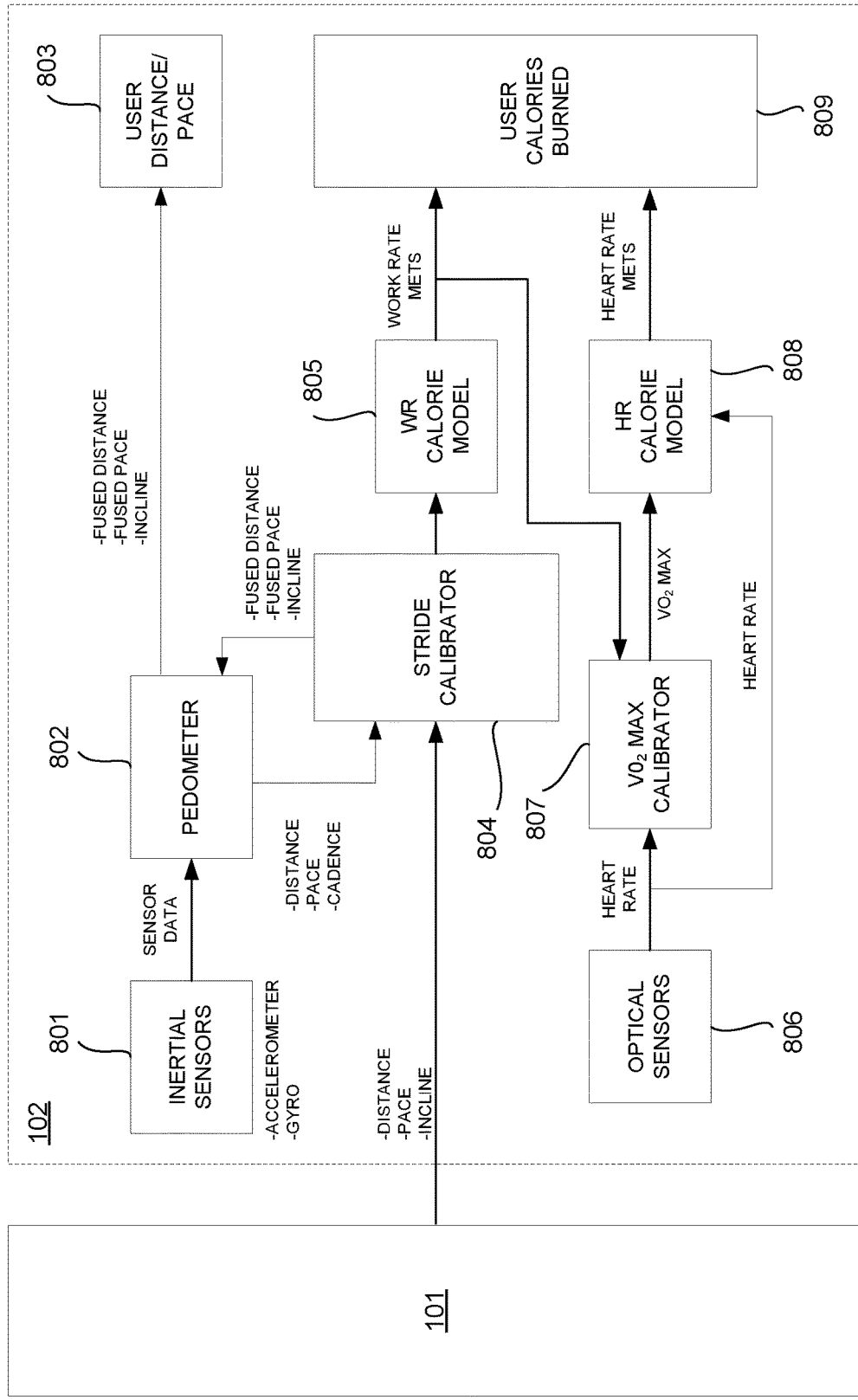
FIG. 8A is a block diagram of a data flow performed by a wearable computer for determining calories burned based on data from a treadmill, according to an embodiment.

FIG. 8A is a block diagram of data flow for determining caloric expenditure based on treadmill data, according to an embodiment. System 800 includes fitness machine 101 in wireless communication with wearable computer 102, which operate as described in reference to FIGS. 1-7. Wearable computer 102 includes software that implements the data flow. In the example shown, fitness machine 101 is a treadmill and provides treadmill data (e.g., distance, pace, incline) calculated by a treadmill computer to wearable computer 102.

Wearable computer 102 includes one or more inertial sensors 801 (e.g., an accelerometer, gyroscope) that provide sensor data (e.g., accelerations, angular rates) to digital pedometer 802. Digital pedometer 802 uses the sensor data to determine a step count of the user. Stride calibrator 804 calculates a calibration factor based on the treadmill data (e.g., considered truth data) and the pedometer output data (e.g., considered estimated data). The calibration factor is applied to the pedometer output data, and the calibrated pedometer output data is displayed as workout session data on a display of wearable computer 102, or sent back to treadmill 101 for display, or sent to another device for display or storage.

In an embodiment, stride calibrator 804 calculates a calibrated stride length that is input into work rate calorie model 805. A work rate can be calculated for each type of fitness machine. For treadmill 101, the applied power output or work rate (WR) can be calculated using the treadmill data. Generically, WR=f(energy the machine is calculating), where f(.) denotes a function of the parameter(s) within parentheses. For a treadmill, WR=f(pace)*g(grade correction), and for a stationary bike WR=f(speed)*g(resistance). In the example shown, work rate calorie model 805 calculates the caloric expenditure (in METs) of the user based on the work rate calculated using the treadmill data (e.g., using pace and grade). The work rate METs can then be input into $VO_2$ max calibrator 807 as an implicit estimate of $VO_2$. Optical sensors 806 in wearable computer 102 provide heart rate data as another input into $VO_2$ Max calibrator 807. $VO_2$ max calibrator 807 uses the implicit estimate of $VO_2$ and the heart rate data to calibrate $VO_2$ max. The heart rate data and the calibrated $VO_2$ max are then input into heart rate calorie model 808. Heart rate calorie model 808 calculates the caloric expenditure (in METs) of the user based on the user's heart rate data and the calibrated $VO_2$ max. The work rate METs and the heart rate METs can be displayed as workout session data on wearable computer 102 or sent back over the communication connection to treadmill 101 to be displayed, or can be sent to another device for display or storage.

In an embodiment, WR and HR calorie expenditure values (MET values) are estimated over successive, non-overlapping intervals of time referred to herein as "epochs." In an embodiment, an "epoch" can be x seconds (e.g., 2.56 seconds, corresponding to 256 samples of accelerometer sensor data sampled at 100 Hz). Over each epoch, a single MET value is reported, which is the best estimate of METs expended by the user. This best MET estimate is chosen by arbitration logic which compares the magnitude of the MET values for work rate and heart rate, and the confidence associated with each of those values. For example, the heart rate MET value could be preferred if it is greater than the work rate MET value by x % (e.g., 10%). As an example, the user exertion on an incline could be under-estimated by work rate METs but tracked more accurately by heart rate METs.

In an embodiment, two calibration methods are implemented by calibrator 804: a cadence-based look-up table and an accelerometer-energy method. The cadence-based look-up table includes cadence and stride length (SL), where cadence=Steps/unit_time, SL=D/Steps, Steps is the step count calculated by wearable computer 102 and D is the truth distance received from the treadmill. In an embodiment, Steps is measured by wearable computer 102 using sensor data. Under a constant cadence, cadence is highly correlated with SL. When the user is not on treadmill 101, wearable computer 102 can use the current cadence to look-up SL from the cadence-based look-up table.

In the accelerometer-energy method, wearable computer 102 calculates an uncalibrated SL (SL_uncal) based on a function of the acceleration data (SL_uncal=f(accel)). An uncalibrated distance (D_uncalibrated) is then calculated from Steps and SL_uncal, such that D_uncalibrated=Steps*SL_uncal and Pace uncalibrated=time/(Steps*SL_uncal). While the user is on treadmill 101, a calibration factor is calculated as Kval=D/D_uncalibrated. When the user is off treadmill 101, D_calibrated=Steps*SL_uncal*Kval. For both the cadence-based look-up table and the accelerometer-energy method, grade can be included. Also, a separate cadence-based look-up table can be used for walking and running.

Any desired model can be used for work rate calorie model 805. In an embodiment, a quadratic model can be used for walking and a linear model for running, where a switch from the quadratic model to the linear model at a specified speed (e.g., 4.5 mph) and the quadratic model is based on the user's height. The quadratic model accounts for the difference in stride length when transitioning from walking to running. In an embodiment, walking METs are computed as: METs=k*(a*s$^2$+b*s+c), where s=speed in miles/hour, k is a grade correction factor, such that k=1 on flat (zero uphill grade) and k>1 if uphill grade is detected, and a, b, c are constants that can be determined empirically. Run METs are computed as: METs=k*(a*s+c). The speed at which the model switches from walk to run METs is determined in the range of 4.2-4.8 miles/hour as a function of the user's height.

Any desired model can be used for heart rate calorie model 808. In an embodiment, HR calorie model 808 linearly scales VO$_2$ max output from VO$_2$ max calibrator 807 by a fractional heart rate (heart rate normalized by the user's observed minimum and maximum heart rates). VO$_2$ max can be estimated using any known method. For example, using Uth-Sørensen-Overgaard-Pedersen estimation VO$_2$ max can be estimated using the following equation.

$$VO_2max \approx \frac{HR_{max}}{HR_{rest}} \times 15.3 \frac{mL}{kg \cdot minute} \times 15.3 \text{ mL/kg},$$

where $HR_{max}$ is the maximum heart rate and $HR_{rest}$ is the resting heart rate.

Figure 8B:
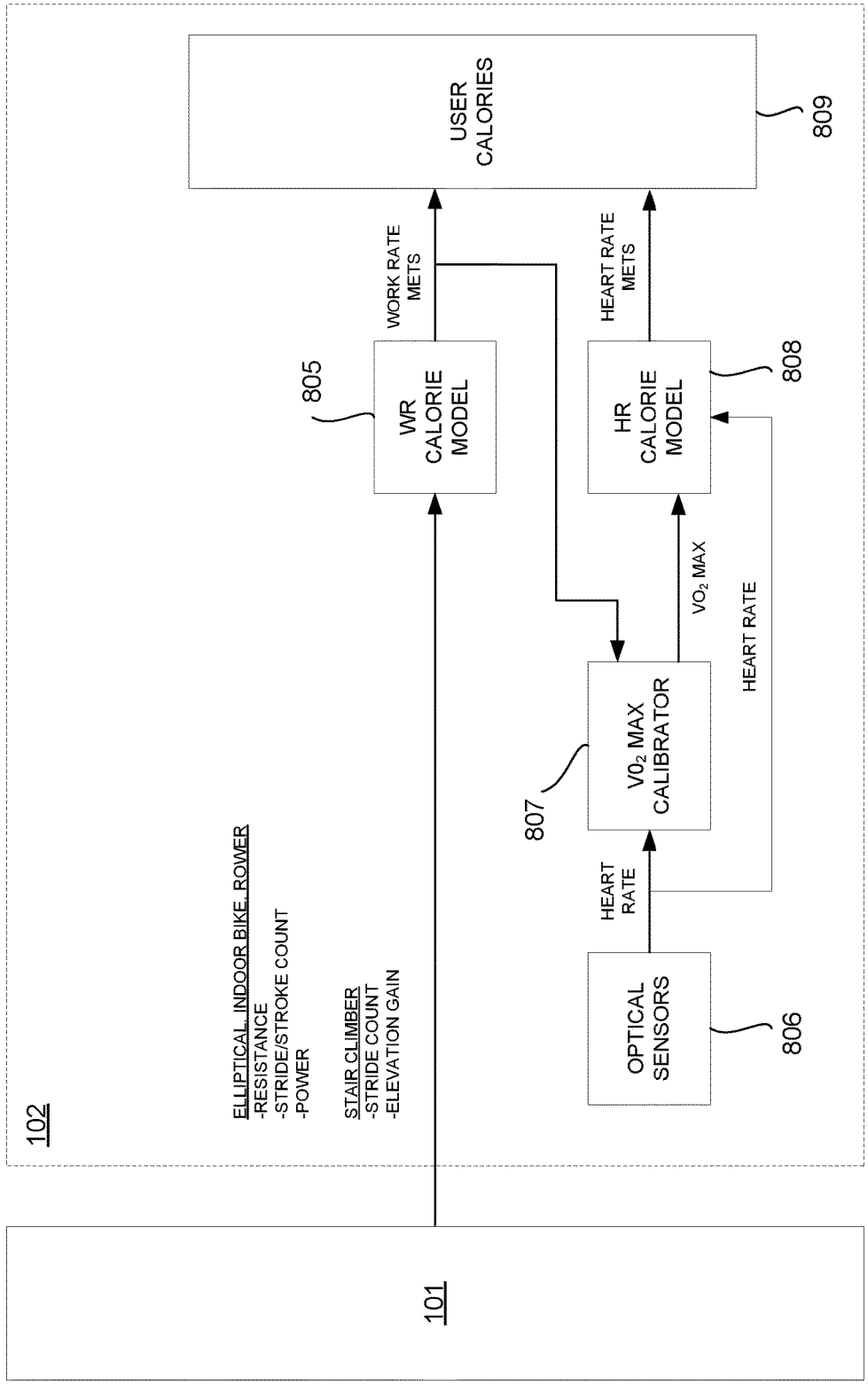
FIG. 8B is a block diagram of a data flow performed by a wearable computer for determining calories burned based on data from an elliptical, indoor bike, rower or stair climber, according to an embodiment.

FIG. 8B is a block diagram of a data flow performed by a wearable computer for determining calories burned based on data from an elliptical, indoor bike, rower or stair climber, according to an embodiment. System 800 includes fitness machine 101 in wireless communication with wearable computer 102, which operate as described in reference to FIGS. 1-7. Wearable computer 102 includes software that implements the data flow.

WR calorie model 805 takes as input fitness machine data and outputs an estimate of work rate (in METs). The details of the treadmill WR calorie model were previously described above. If fitness machine 101 is an elliptical, indoor cycle or rower, than fitness machine data includes resistance, stride/stroke count and power. If the fitness machine 101 is a stair climber, the fitness machine data includes stride count and elevation gain. For an indoor cycle, METs are a linear function of the power (normalized by user weight). In an embodiment, METs=a*normalized_power+c, and power is a function of user-selected resistance level and cadence, and user weight. Elliptical and rower METs are a function of power, cadence and resistance level, similar to the indoor cycle. Stair climber METs are a function of elevation gain and step cadence.

Example Process

Figure 9:
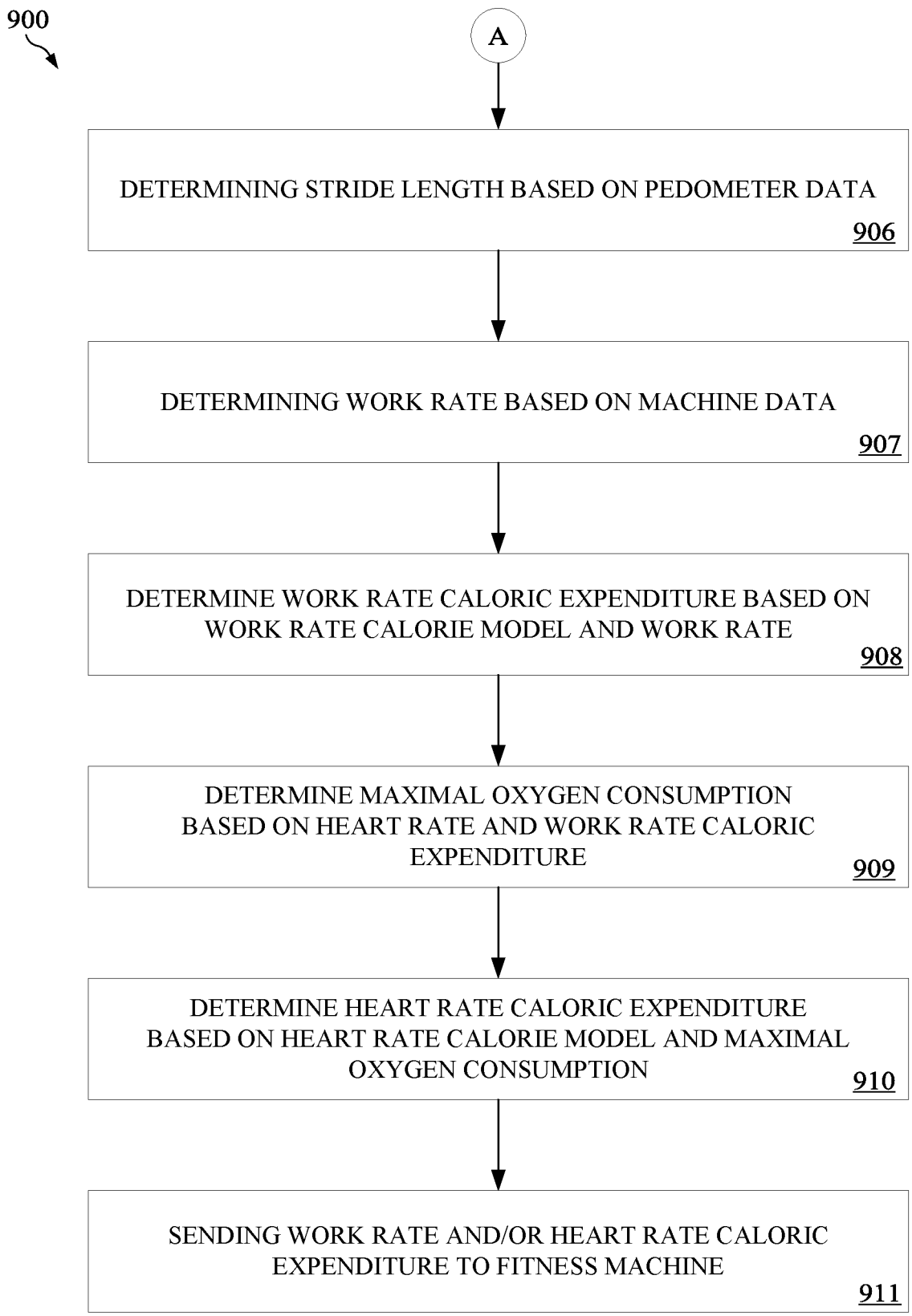
FIG. 9 is a flow diagram of an example process performed by a wearable computer to determine calories burned based on machine data from a fitness machine, according to an embodiment.

FIG. 9 is a flow diagram of an example process 900 performed by a wearable computer to determine calories burned based on data from a treadmill, according to an embodiment. Process 900 can be implemented using the wearable computer architecture 1000 disclosed in reference to FIG. 10.

Process 900 begins by establishing, by a processor of a wireless wearable computer worn by a user, a wireless communication connection with a fitness machine (901). Process 900 continues by obtaining, by the processor using the communication connection, machine data from the fitness machine while the user is engaged in a workout session on the fitness machine (902). Process 900 continues by obtaining, from one or more motion sensors of the wireless wearable device, motion data generated in response to motion of the user on the fitness machine (903). Process 900 continues by obtaining, from a heart rate sensor of the wireless device, heart rate data of the user (904). Process 900 continues by determining, by a digital pedometer of the wearable computer, pedometer output data based on the motion data (905). Process 900 continues by determining, by the processor, a stride length of the user based on the pedometer output data and the machine data (906). Process 900 continues by determining, by the processor, a work rate based on the machine data (907). Process 900 continues by determining, by the processor, a work rate caloric expenditure by applying a work rate calorie model to the work rate (908). Process 900 continues by determining, by the processor, a maximal oxygen consumption of the user based on the heart rate data and the work rate caloric expenditure (909). Process 900 continues by determining, by the processor, a heart rate caloric expenditure by applying a heart rate calorie model to the heart rate data and the maximal oxygen consumption (910). Process 900 continues by sending, by the processor to the treadmill via the communication connection, at least one of the work rate caloric expenditure or the heart rate caloric expenditure (911).

Exemplary Wearable Computer Architecture

Figure 10:
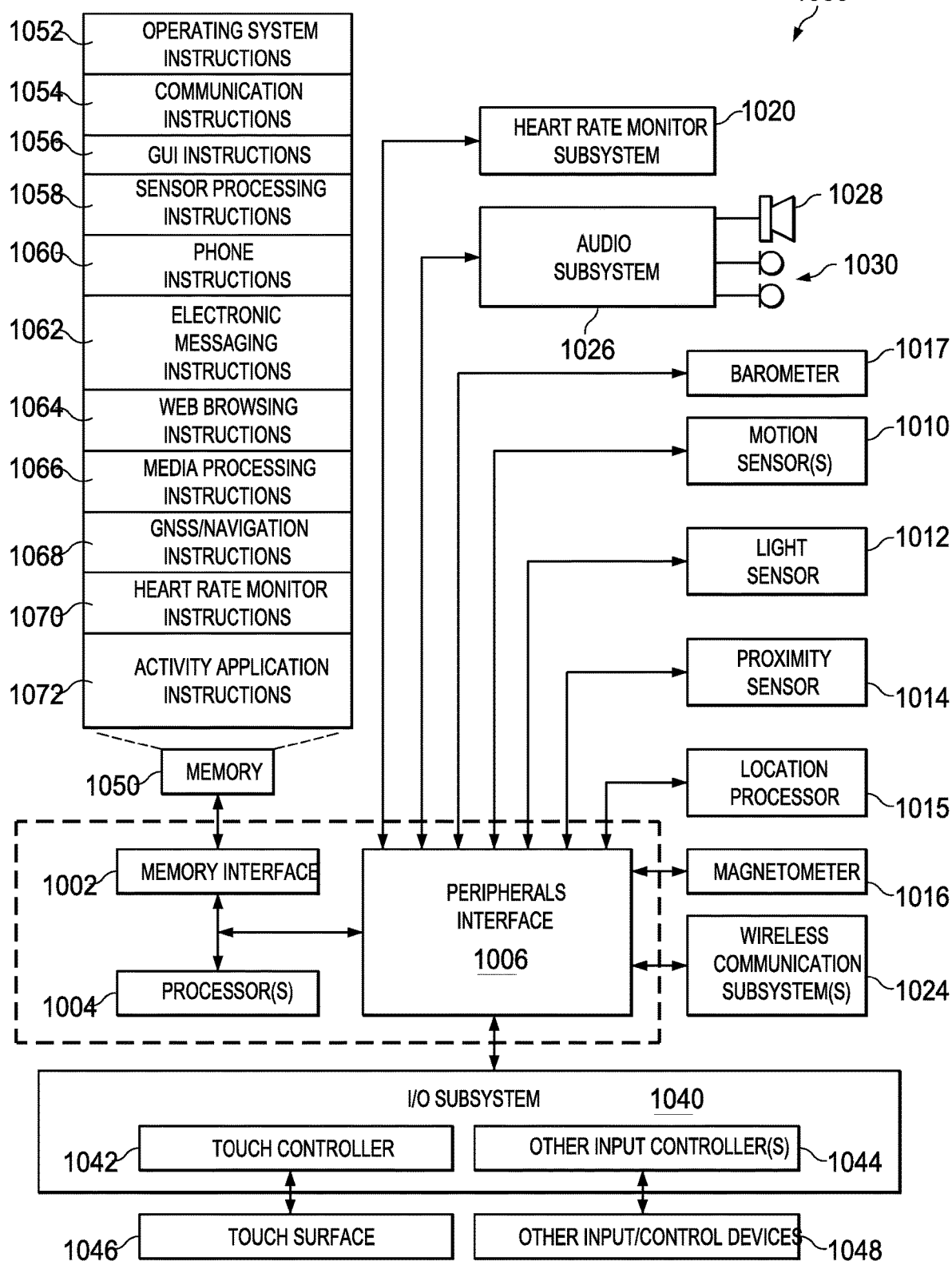
FIG. 10 is example wearable computer architecture for a wearable computer implementing the features and operations described in reference to FIGS. 1-9.

FIG. 10 illustrates example wearable computer architecture 1000 implementing the features and operations described in reference to FIGS. 1-9. Architecture 1000 can include memory interface 1002, one or more data processors, image processors and/or processors 1004 and peripherals interface 1006. Memory interface 1002, one or more processors 1004 and/or peripherals interface 1006 can be separate components or can be integrated in one or more integrated circuits.

Sensors, devices and subsystems can be coupled to peripherals interface 1006 to provide multiple functionalities. For example, one or more motion sensors 1010, light sensor 1012 and proximity sensor 1014 can be coupled to peripherals interface 1006 to facilitate motion sensing (e.g., acceleration, rotation rates), lighting and proximity functions of the wearable computer. Location processor 1015 can be connected to peripherals interface 1006 to provide geo-positioning. In some implementations, location processor 1015 can be a GNSS receiver, such as the Global Positioning System (GPS) receiver. Electronic magnetometer 1016 (e.g., an integrated circuit chip) can also be connected to peripherals interface 1006 to provide data that can be used to determine the direction of magnetic North. Electronic magnetometer 1016 can provide data to an electronic compass application. Motion sensor(s) 1010 can include one or more accelerometers and/or gyros configured to determine change of speed and direction of movement of the wearable computer. Barometer 1017 can be configured to measure atmospheric pressure around the mobile device.

Heart rate monitoring subsystem 1020 for measuring the heartbeat of a user who is wearing the computer on their wrist. In an embodiment, subsystem 1020 includes LEDs paired with photodiodes for measuring the amount of light reflected from the wrist (not absorbed by the wrist) to detect a heartbeat.

Communication functions can be facilitated through wireless communication subsystems 1024, which can include radio frequency (RF) receivers and transmitters (or transceivers) and/or optical (e.g., infrared) receivers and transmitters. The specific design and implementation of the communication subsystem 1024 can depend on the communication network(s) over which a mobile device is intended to operate. For example, architecture 1000 can include communication subsystems 1024 designed to operate over a GSM network, a GPRS network, an EDGE network, a Wi-Fi™ network and a Bluetooth™ network. In particular, the wireless communication subsystems 1024 can include hosting protocols, such that the mobile device can be configured as a base station for other wireless devices.

Audio subsystem 1026 can be coupled to a speaker 1028 and a microphone 1030 to facilitate voice-enabled functions, such as voice recognition, voice replication, digital recording and telephony functions. Audio subsystem 1026 can be configured to receive voice commands from the user.

I/O subsystem 1040 can include touch surface controller 1042 and/or other input controller(s) 1044. Touch surface controller 1042 can be coupled to a touch surface 1046. Touch surface 1046 and touch surface controller 1042 can, for example, detect contact and movement or break thereof using any of a plurality of touch sensitivity technologies, including but not limited to capacitive, resistive, infrared and surface acoustic wave technologies, as well as other proximity sensor arrays or other elements for determining one or more points of contact with touch surface 1046. Touch surface 1046 can include, for example, a touch screen or the digital crown of a smart watch. I/O subsystem 1040 can include a haptic engine or device for providing haptic feedback (e.g., vibration) in response to commands from processor 1004. In an embodiment, touch surface 1046 can be a pressure-sensitive surface.

Other input controller(s) 1044 can be coupled to other input/control devices 1048, such as one or more buttons, rocker switches, thumb-wheel, infrared port and USB port The one or more buttons (not shown) can include an up/down button for volume control of speaker 1028 and/or microphone 1030. Touch surface 1046 or other controllers 1044 (e.g., a button) can include, or be coupled to, fingerprint identification circuitry for use with a fingerprint authentication application to authenticate a user based on their fingerprint(s).

In one implementation, a pressing of the button for a first duration may disengage a lock of the touch surface 1046; and a pressing of the button for a second duration that is longer than the first duration may turn power to the mobile device on or off. The user may be able to customize a functionality of one or more of the buttons. The touch surface 1046 can, for example, also be used to implement virtual or soft buttons.

In some implementations, the mobile device can present recorded audio and/or video files, such as MP3, AAC and MPEG files. In some implementations, the mobile device can include the functionality of an MP3 player. Other input/output and control devices can also be used.

Memory interface 1002 can be coupled to memory 1050. Memory 1050 can include high-speed random access memory and/or non-volatile memory, such as one or more magnetic disk storage devices, one or more optical storage devices and/or flash memory (e.g., NAND, NOR). Memory 1050 can store operating system 1052, such as the iOS operating system developed by Apple Inc. of Cupertino, Calif. Operating system 1052 may include instructions for handling basic system services and for performing hardware dependent tasks. In some implementations, operating system 1052 can include a kernel (e.g., UNIX kernel).

Memory 1050 may also store communication instructions 1054 to facilitate communicating with one or more additional devices, one or more computers and/or one or more servers, such as, for example, instructions for implementing a software stack for wired or wireless communications with other devices. Memory 1050 may include graphical user interface instructions 1056 to facilitate graphic user interface processing; sensor processing instructions 1058 to facilitate sensor-related processing and functions; phone instructions 1060 to facilitate phone-related processes and functions; electronic messaging instructions 1062 to facilitate electronic-messaging related processes and functions; web browsing instructions 1064 to facilitate web browsing-related processes and functions; media processing instructions 1066 to facilitate media processing-related processes and functions; GNSS/Location instructions 1068 to facilitate generic GNSS and location-related processes and instructions; and heart rate instructions 1070 to facilitate hear rate measurements. Memory 1050 further includes activity application instructions for performing the features and processes described in reference to FIGS. 1-9.

Each of the above identified instructions and applications can correspond to a set of instructions for performing one or more functions described above. These instructions need not be implemented as separate software programs, procedures, or modules. Memory 1050 can include additional instructions or fewer instructions. Furthermore, various functions of the mobile device may be implemented in hardware and/or in software, including in one or more signal processing and/or application specific integrated circuits.

The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., SWIFT, Objective-C, C#, Java), including compiled or interpreted languages, and it can be deployed in any form, including as a stand-alone program or as a module, component, subroutine, a browser-based web application, or other unit suitable for use in a computing environment.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

As described above, some aspects of the subject matter of this specification include gathering and use of data available from various sources to improve services a mobile device can provide to a user. The present disclosure contemplates that in some instances, this gathered data may identify a particular location or an address based on device usage. Such personal information data can include location-based data, addresses, subscriber account identifiers, or other identifying information.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

In the case of advertisement delivery services, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publically available information.

What is claimed is:

1. A method comprising:
   establishing, using one or more processors of a wireless wearable computer worn by a user, a wireless communication connection with a fitness machine;
   obtaining, using the one or more processors using the communication connection, machine data from the fitness machine while the user is engaged in a workout session on the fitness machine;
   obtaining, using one or more motion sensors of the wireless wearable computer, motion data generated in response to motion of the user on the fitness machine;
   determining, using a digital pedometer of the wearable computer, pedometer output data based on the motion data;
   determining, using the one or more processors, a calibrated stride length of the user using the pedometer output data and the machine data;
   determining, using the one or more processors, a work rate caloric expenditure, the work rate caloric expenditure determined using a work rate caloric model with the calibrated stride length as input;
   obtaining, using a heart rate sensor of the wireless wearable computer, heart rate data of the user;
   determining, using the one or more processors, a calibrated maximal oxygen consumption of the user based on the heart rate data and the work rate caloric expenditure;
   determining, using the one or more processors, a heart rate caloric expenditure by applying a heart rate calorie model to the heart rate data and the calibrated maximal oxygen consumption of the user; and
   sending, using the one or more processors, to the fitness machine or other device using the communication connection, at least one of the work rate caloric expenditure or the heart rate caloric expenditure.

2. The method of claim 1, wherein the machine data includes at least one of distance, pace or cadence.

3. The method of claim 1, wherein the fitness machine is a treadmill and the machine data includes at least one of speed, pace, incline, grade or distance traveled.

4. The method of claim 1, wherein the fitness machine is a stationary bike or rower and the machine data includes at least one of resistance, stride length, stroke count or power.

5. The method of claim 1, wherein the fitness machine is a stair climber and the fitness data includes at least one of stride count or elevation gain.

6. The method of claim 1, wherein the work rate and heart rate MET are estimated over successive, non-overlapping intervals of time.

7. The method of claim 1, wherein sending, by the one or more processors to the fitness machine via the communication connection, at least one of the work rate caloric expenditure or the heart rate caloric expenditure, further comprises:
   comparing magnitudes of the work rate and heart calorie expenditure values; and
   sending to the fitness machine the calorie expenditure with the largest magnitude as user calories burned.

8. The method of claim 1, wherein a quadratic work rate calorie model is used for walking and a linear work rate calorie model is used for running.

9. The method of claim 8, wherein the linear model is invoked at a specified speed of the user and the quadratic model is based on the user's height.

10. A wireless wearable computer, comprising:
one or more motion sensors;
a heart rate sensor;
one or more processors;
memory storing instructions that when executed by the one or more processors, cause the one or more processors to perform operations comprising:
  establishing a wireless communication connection with a fitness machine;
  obtaining, using the communication connection, machine data from the fitness machine while a user is engaged in a workout session on the fitness machine;
  obtaining, using the one or more motion sensors, motion data generated in response to motion of the user on the fitness machine;
  determining digital pedometer output data based on the motion data;
  determining a calibrated stride length of the user using the pedometer output data and the machine data;
  determining a work rate caloric expenditure, the work rate caloric expenditure determined using a work rate caloric model with the calibrated stride length as input;
  obtaining, using the heart rate sensor, heart rate data of the user;
  determining a calibrated maximal oxygen consumption of the user based on the heart rate data and the work rate caloric expenditure;
  determining a heart rate caloric expenditure by applying a heart rate calorie model to the heart rate data and the calibrated maximal oxygen consumption of the user; and
  sending to the fitness machine or other device using the communication connection, at least one of the work rate caloric expenditure or the heart rate caloric expenditure.

11. The wireless wearable computer of claim 10, wherein the machine data includes at least one of distance, pace or cadence.

12. The wireless wearable computer of claim 10, wherein the fitness machine is a treadmill and the machine data includes at least one of speed, pace, incline, grade or distance traveled.

13. The wireless wearable computer of claim 10, wherein the fitness machine is a stationary bike or rower and the machine data includes at least one of resistance, stride length, stroke count or power.

14. The wireless wearable computer of claim 10, wherein the fitness machine is a stair climber and the fitness data includes at least one of stride count or elevation gain.

15. The wireless wearable computer of claim 10, wherein the work rate and heart rate MET are estimated over successive, non-overlapping intervals of time.

16. The wireless wearable computer of claim 10, wherein sending to the fitness machine, via the communication connection, at least one of the work rate caloric expenditure or the heart rate caloric expenditure, further comprises:
  comparing magnitudes of the work rate and heart calorie expenditure values; and
  sending to the fitness machine the calorie expenditure with the largest magnitude as user calories burned.

17. The wireless wearable computer of claim 10, wherein a quadratic work rate calorie model is used for walking and a linear work rate calorie model is used for running.

18. The wireless wearable computer of claim 17, wherein the linear model is invoked at a specified speed of the user and the quadratic model is based on the user's height.

* * * * *